US012213797B2

(12) United States Patent
Stepien et al.

(10) Patent No.: US 12,213,797 B2
(45) Date of Patent: Feb. 4, 2025

(54) APPARATUS FOR MULTIMODAL ANALYSIS OF ALLERGIC REACTIONS IN SKIN TESTS AND A HYBRID METHOD FOR MULTISPECTRAL IMAGING OF ALLERGIC REACTIONS IN SKIN TESTS AND ITS USE FOR AUTOMATIC EVALUATION OF THE RESULTS OF THESE TESTS

(71) Applicant: MILTON ESSEX SA, Warsaw (PL)

(72) Inventors: Jacek Stepien, Warsaw (PL); Radoslaw Solan, Warsaw (PL); Pawel Lukasiewicz, Warsaw (PL)

(73) Assignee: MILTON ESSEX SA, Warsaw (PL)

( * ) Notice: Subject to any disclaimer, the term of this patent is extended or adjusted under 35 U.S.C. 154(b) by 1127 days.

(21) Appl. No.: 17/047,768

(22) PCT Filed: Apr. 23, 2019

(86) PCT No.: PCT/EP2019/060315
§ 371 (c)(1),
(2) Date: Oct. 15, 2020

(87) PCT Pub. No.: WO2019/211118
PCT Pub. Date: Nov. 7, 2019

(65) Prior Publication Data
US 2021/0169396 A1    Jun. 10, 2021

(30) Foreign Application Priority Data
Apr. 30, 2018    (PL) .......................................... 425395

(51) Int. Cl.
*A61B 5/00*    (2006.01)
*A61B 5/01*    (2006.01)
(Continued)

(52) U.S. Cl.
CPC ............ *A61B 5/411* (2013.01); *A61B 5/0064* (2013.01); *A61B 5/0077* (2013.01); *A61B 5/015* (2013.01);
(Continued)

(58) Field of Classification Search
CPC ..... A61B 5/411; A61B 5/0064; A61B 5/0077; A61B 5/015; A61B 5/0261; A61B 5/445;
(Continued)

(56) References Cited

U.S. PATENT DOCUMENTS

| 11,013,414 B2 * | 5/2021 | Yao ...................... A61B 5/0082 |
| 2008/0077019 A1 * | 3/2008 | Xiao ..................... G06T 7/0012 |
|  |  | 600/474 |

(Continued)

FOREIGN PATENT DOCUMENTS

JP    2004267308 A  *  9/2004  ........... A61B 5/0059

OTHER PUBLICATIONS

Google Machine translation of JP2004267308A (Year: 2004).*
(Continued)

*Primary Examiner* — Rene T Towa
*Assistant Examiner* — Justin Xu
(74) *Attorney, Agent, or Firm* — Dickinson Wright PLLC; Andrew D. Dorisio

(57) ABSTRACT

A multimodal apparatus for analysis of allergic reactions during skin tests and a method of multispectral imaging of allergic reactions in case of the type I and the type IV allergic reactions induced by performing skin allergy Prick and Patch tests combine thermal imaging with Laser Doppler flowmetry or 3D scanning to confirm the results of epidermal hyperthermia tests.

4 Claims, 1 Drawing Sheet

(51) Int. Cl.
*A61B 5/026* (2006.01)
*G01B 11/25* (2006.01)

(52) U.S. Cl.
CPC ............ *A61B 5/0261* (2013.01); *A61B 5/445* (2013.01); *A61B 2560/0223* (2013.01); *A61B 2560/0406* (2013.01)

(58) Field of Classification Search
CPC .... A61B 2560/0223; A61B 2560/0406; G01B 11/2518
See application file for complete search history.

(56) References Cited

U.S. PATENT DOCUMENTS

| | | | |
|---|---|---|---|
| 2010/0172567 A1* | 7/2010 | Prokoski | A61B 5/411 348/47 |
| 2012/0078113 A1* | 3/2012 | Whitestone | A61B 5/015 600/474 |
| 2015/0054922 A1 | 2/2015 | Fisker et al. | |
| 2015/0198797 A1 | 7/2015 | Andre et al. | |
| 2016/0367152 A1* | 12/2016 | Stepien | G01K 13/20 |
| 2017/0245792 A1* | 8/2017 | Tversky | A61B 5/445 |

OTHER PUBLICATIONS

Justo et al. (Year: 2016).*
Rokita et al. (Year: 2011).*
X. Justo et al. : "Prick test: evolution towards automated reading", Allergy, vol. 71, No. 8, Apr. 21, 2016, United Kingdom.

* cited by examiner

APPARATUS FOR MULTIMODAL ANALYSIS OF ALLERGIC REACTIONS IN SKIN TESTS AND A HYBRID METHOD FOR MULTISPECTRAL IMAGING OF ALLERGIC REACTIONS IN SKIN TESTS AND ITS USE FOR AUTOMATIC EVALUATION OF THE RESULTS OF THESE TESTS

FIELD OF THE INVENTION

The subject of invention is an apparatus for multimodal analysis of allergic reactions in skin tests and a method of multispectral imaging of allergic reactions during the type I and the type IV allergic reactions induced by application of allergenic substances in skin allergy Prick tests and Patch tests.

BACKGROUND ART

According to the World Health Organization (WHO), allergy ranks third on the list of the most common chronic diseases and is considered one of so-called lifestyle diseases, the elimination of which is currently an international priority both for health care institutions and individual governments. The WHO described the $21^{st}$ century as the age of allergy epidemic (WHO: White Book on Allergy, 2011-2012). WHO experts estimate that the number of population members suffering from allergy increases annually by 0.5 to 2.5%. As far as new incidences are concerned, none of the other lifestyle diseases is growing at such a rate. Precise instrumental diagnosis in form of allergic tests is the first step to effective treatment. It is a challenge to provide patients with easy access to diagnostics as well as to adapt diagnostic tools in order to automate and standardize the test procedure. The World Allergy Organization (WAO) recognizes skin allergy tests as a gold standard for allergy diagnosis, recommends using them as a reference method that replicate the factual allergic reactivity of the patient's body to tested allergenic substances.

In clinical practice, two different types of skin allergy tests are currently used:

Prick tests in different variants, comprising superficial puncturing of the patient's skin and application of tested allergenic substances (allergens); these tests are used to examine type I allergic reaction (immediate hypersensitivity), mainly to inhalant and food allergens;

Patch tests comprising application of tested substances (haptens) directly on undamaged skin using a special patch worn by the patient wears for at least 48 hours; these tests are used to determine a type IV allergic reaction (delayed hypersensitivity), occurring during allergic contact dermatitis, including occupational allergies of various types.

A problem common for both types of skin tests is the reading method, since both Prick and Patch tests are currently evaluated by a physician exclusively on the basis of symptoms visible at the skin surface and employing visual assessment technique by means of a simple ruler with a millimeter scale. In case of Prick tests, the reading involves measuring the size allergic weal and comparing it to the weal size at the histamine control area (exposed to histamine hydrochloride) as well as measuring the size of allergic erythema, and subsequently the results are marked on different variants of the point-based grading scale. In case of Patch tests, in addition to assessing the presence of allergic erythema, a physician also assesses the presence of non-specific symptoms in form of papules and/or vesicles appearing at the site of application of the test substance, with the results being also marked on a point-based grading scale.

The method of visual reading of skin tests, both Prick and Patch tests, based on non-specific skin symptoms observed by a physician, does not ensure repeatability of readings, and therefore does not provide the necessary standardization and does not meet the criteria of evidence-based-medicine (EBM), requiring so-called markers, determined on the basis of measurable biochemical or biophysical quantitative indicators, for subsequent evaluation. Visual method is an author technique, affected by an unknown level of false positive and false negative readings.

From WO 2016/064795 A1 a device for skin test reading is known, provided with a housing and with a short-wave infrared detector (SWIR). The SWIR detector can be provided with a lens allowing to record an image of the patient's skin test area and is configured to detect skin lesions (vesicles, pustules) in this test area following topical application of an allergen.

WO 2016/096591 A1 describes a method of allergy detection in a patient during a skin test, said method comprising: recording two sets of radiation intensity values in a spatial layout over the area of patient's skin where the allergen was applied—for visible and infrared radiation, followed by generating two corresponding sets of spatial distribution of pulse wave amplitudes in a photoplethysmogram (PPG), comparing them with each other and with the test skin area, and determination on this basis whether the patient is showing an allergic reaction to the tested allergen.

WO2014182932 A1 discloses a method of testing specificity and intensity of an allergic reaction by puncturing the patient's skin with a system of microneedles containing multiple epitopes, followed by determining the skin reaction to these allergens. The reaction is measured by means of a thermal imaging camera, and analysis and selection of a possible therapy is performed based on these results.

US 2012253224 A1 describes an apparatus for performing skin allergy tests, provided with a housing having a hole marking the tested area over the patient's skin and a camera to record the tested area image, a light-emitting element, a device attaching the apparatus to the patient's arm and an image processing controller.

US 20170007170 A1 describes a device for performing skin allergy tests, comprising an adhesive carrier strip affixable to the skin, which on its underside is provided with microneedles for introducing the allergen into punctures. The analysis is based on an image comparison of the patient's skin surface area before and after the application of the strap, followed by an electronic analysis of both images.

Further, WO 2013116316 A1 discloses a hyperspectral imaging system with at least one hyperspectral imaging unit containing: lenses for directing diffused light, reflected light or light passing through the tested object to a hyperspectral filter system separating the light into discrete spectral bands; a sensor recording this radiation and generating appropriate electrical signals corresponding to the tested object; and at least one processor to determine biological parameters based on the data coming from the hyperspectral image.

WO 2014140215 A1 describes methods and apparatus for measuring the size of vesicles and detecting allergies in three-dimensional representations of forearms' area. The apparatus performs a three-dimensional scan of an arm with vesicles, and as a result of digital processing, a three-dimensional representation of particular vesicle is obtained, forming the basis for diagnosing of an allergic reaction.

US 20040176701 A1 discloses a device for testing type IV allergic reactions, using comparative measurement of the laser beam scattered by blood cells found in blood vessels of a skin area not exposed to the allergen and of the exposed area.

PL 410688 A1 is related to a contact thermo-optical system and its use for non-invasive imaging of the size of histamine-induced subcutaneous hyperthermal reaction in a skin allergic reaction. The operation of the system is based on registering color changes of a thermo-optical system based on liquid crystalline mixtures changing conformation in response to local hyperthermia triggered by an allergic reaction. Liquid crystalline contact thermography described in this document is a thermal imaging technique, but unlike other solutions based on remote (emission) thermal imaging using an infrared thermal imaging camera, it allows for lossless representation of an allergic hyperthermic reaction on the skin surface at a scale of 1:1.

Further, US 2018014734 A1 describes a device for the analysis of human tissue, in particular skin, in terms of heat transfer (including thermal conductivity, thermal diffusivity, thermal capacity). The device includes elements supplying heat to a tissue and detectors recording the spatial and temporal distribution of physiological parameters or physical properties of the tissue influenced by heat. This information may be correlated with the rate and/or direction of blood flow, presence of vascular occlusion, circulatory changes associated with inflammatory reactions, level of hydration and other physiological parameters.

US 2010121200 A1 discloses a device designed to support the diagnosis of pathophysiological tissue changes, in particular burns, using thermal imaging devices, vascular scintigraphy techniques or laser Doppler flowmetry to highlight local changes in blood flow.

US 2017035344 A1 relates to an allergy detection systems using thermal face measurements, including a frame with a thermal imaging camera mounted on the patient's head less than 10 cm from the patient's face and configured to record a thermal image of at least part of the patient's nose, which after digital processing forms the basis for determining the size of allergic reaction.

Moreover, U.S. Pat. No. 4,819,657 B1 relates to an automatic allergy detection system containing an electrode provided with an electronic system and a device for transdermal delivery of allergens to the patient's body. The electrode is also provided with a temperature sensor to measure the temperature of the skin area adjacent to the allergen administration site. The measurement is carried out every 30 seconds for a period of 15 minutes and the results are presented to a physician in a graphical form.

US 20040019269 A1 discloses a method for early detection of inflammation and infection in animals using infrared thermography.

Finally, US 2008269635 A1 describes an allergy testing system featuring a microneedle puncture system, capsules containing allergens to be administered into the punctures, and an imaging system with sensors to determine the topographic profile of the allergic reaction at the puncturing site.

Development of imaging techniques, including thermal imaging using cameras operating in various infrared bands, allows for revealing specific thermal signatures appearing in the skin tissue as a result of a developing allergic reaction in response to administered allergens or haptens (test substances). The key technical problem is the relatively low geometric or spatial resolution of used cameras, resulting in difficulties in precise, topographical identification of a particular allergen's application site on a thermal image. An additional problem in Patch tests is constituted by the presence of different types of skin symptoms in form of papules and vesicles formed as a result of an allergic reaction, since for physicians they constitute a fundamental differentiating variable of strong positive reaction from a negative one. In the infrared imaging of a hyperthermic allergic reaction in Patch tests, such a difference in reaction intensity also should be adequately reflected, which requires visualization of a much denser map of epidermal distribution of isotherms over the skin area, especially when digital zooming is applied. The problem with reliability of measurements and the resolution of thermal imaging cameras at the skin level, arises from too wide temperature range of infrared cameras, covering more than 100° C., and with average measurement error of approximately ±2%, that causes possible erroneous result at the level of approximately +/−2° C., which is more than the absolute value of allergic hyperthermia. Moreover, the technical limitations of the cameras, despite their nominal parameters, are such that at microbolometer matrix resolution of approximately 320× 240 pixels and thermal resolution of 0.05° C., when the camera (here: e.g. FUR A325 camera) detecting infrared radiation having a wavelength of 7.5-13.0 μm and having a field of view (FOV) of 25°×19°, the instantaneous field of view (iFOV) being 1.36 mrad results in the fact, that at a distance of 1 m from the skin's surface each analytical pixel is as large as 1.36 mm, and an area recommended for thermal analysis is at least 3×3 pixels, which means that the smallest analytical area at the distance of 1 m is as big as 4.08×4.08 mm, which is far too large for allergic skin tests purposes, particularly for Patch tests, where the size of the entire single test area is only 10×10 mm.

These restrictions do not eliminate infrared cameras from medical applications, but to make them provide correct imaging of the scale of the allergic skin response, it is necessary to combine them with additional scanning instruments, to confirm—using other methods—the initial thermal imaging identification of the tested area where the allergic reaction occurred.

To conclude, using an infrared camera highlights anomalies occurring in the course of allergy tests (Dencheva M. et al.; Thermovision in dental allergology, Journ. of IMAB—Annual Proceeding, vol. 20, issue 3, 2014), which appear in form of specific hyperthermal signatures, but does not allow to obtain diagnostic certainty due to technical limitations, in particular because of insufficient thermo-optical and spatial resolution of the cameras, which do not allow to reliably distinguish hyperthermia epicenters, i.e. a physical location of application sites of a specific allergenic substance on thermogram.

Infrared examination with thermal imaging camera requires simultaneous confirmation by another technique—laser Doppler flowmetry (J. Serup J., Staberg B., Quantification of Weal Reactions with Laser Doppler Flowmetry—Comparative Blood Flow Measurements of the Oedematous Centre and the Perilesional Flare of Skin-Prick Histamine Weals, Allergy Europ. Journ. of Allergy and Clinic. Immunology, Vol. 40, Issue 4, 1985) so as to record the image of sites of locally increased blood flow in dilated vessels of skin microcirculation as a result of released histamine in the sites of positive skin test results, as well as by an optical method—scattering, to identify skin lesions distinguishable, in form of erythema, papules and vesicles, when compared to unchanged skin not affected by allergic reaction.

Use of laser Doppler flowmetry aimed to visualize subepidermal sites of allergic reaction characterized by increased local blood flow through dilated microvessels of subpapillary plexuses, is associated almost exclusively with experimental and scientific research. This technique cannot be used as an autonomous method of clinical evaluation of the allergic skin reaction, because it represents only one vascular component of this reaction through the posthistamine effect and requires an additional technique to verify flowmetry by using the same pathophysiological mechanism. The method of laser Doppler flowmetry by definition does not illustrate the complex of phenomena accompanying the skin allergic reaction, and accordingly provides only fragmentary information on the course of skin allergy tests.

Use of instrumental optical methods to evaluate the skin reaction to application of allergens/haptens is ineffective due the same problems as in case of the visual assessment method, because it is based on the analysis of skin symptoms rather than of specific biomarkers. Optical methods focusing on increasing the contrast around the reaction site and isolation of skin anomalies in form of epidermal erythema proved to be insufficient (S. Astner et al., Pilot study on the sensitivity and specificity of in vivo reflectance confocal microscopy in the diagnosis of allergic contact dermatitis; Journal of the American Academy of Dermatology, Vol. 3, Issue 6, December 2005; 986-992) and failed as an autonomous tool for comprehensive assessment of allergic skin reaction. However, they have the analytical potential to differentiate the status of the skin affected by an allergic reaction from unchanged areas, but not by increasing the contrast of the epidermal response or optical enlargement of the skin eruptions, but rather by objective reflectometric analysis of the reflection/absorption coefficients of visible light by healthy skin areas and those changed during the tests, which is particularly important for Patch tests, where, in addition to erythema, it is essential to take into account the formed papules and/or vesicles, which in the biophysical sense constitute an area with different optical characteristics (reflection and absorption in the electromagnetic spectrum width range of 380-700 nm).

Up till now, none of the abovementioned methods of analysis of skin condition aimed to evaluate test allergic reaction has proven autonomously to show clinically confirmed efficiency at a level sufficient to be employed as a single technique for automatic reading of the allergy skin tests in both Prick and Patch tests. The essential novelty adopted in the apparatus according to the invention is the use of hybrid, multispectral imaging allowing to obtain technical redundancy necessary for objective evaluation of the results of infrared skin imaging at the allergy tests areas by combining epidermal thermal imaging with Laser Doppler Flowmetry, in order to confirm the dilation of skin microcirculation vessels induced by the activation of H1 histamine receptors during a type I allergic reaction, and, in the very same device, a combination of epidermal thermal imaging and epidermal reflectometry to confirm skin lesions in form of erythema, papules or vesicles caused by a type IV test allergic reaction.

SUMMARY OF THE INVENTION

The apparatus according to the invention allows for a spectacular improvement of the accuracy and, at the same time the reading reliability of allergy skin tests reproducing both the type I allergic reaction (immediate hypersensitivity) and type IV allergic reaction (delayed hypersensitivity) by introducing multispectral imaging available through a new and unique combination—within one device—of three digital imaging techniques designed not only to analyse the skin surface, but also the structures located deeper, up to approximately 2000 µm in order to identify: (a) thermal anomalies, so-called hyperthermal allergic reaction, (b) skin surface anomalies appearing as so-called epidermal reaction in Patch tests in form of erythema, papules, vesicles and swelling, (c) anomalies located in the deeper layer of the skin in form of dilatation of microvessels of subpapillary plexuses.

As a result of research it was found that the combination of three different techniques: thermal imaging, laser Doppler flowmetry and optical refractometry make it possible to obtain a complete picture of the skin allergic reaction both in Prick and Patch tests.

The object of the invention is an apparatus for multimodal imaging and analysis of biophysical parameters of allergic skin reactions in skin allergy Prick and Patch tests, having a hybrid structure, combining, in a housing open from the bottom, a recording system containing an infrared thermal imaging camera operating and a stationary camera with a CCD or CMOS photosensitive matrix, operating in visible light spectrum (within the electromagnetic wavelength range from 380 nm to 780 nm). The apparatus according to the invention further has a rotating tube comprising a three-dimensional optical scanner (3D) and a vertically retractable Doppler sensor for transdermal laser Doppler flowmetry. The housing includes also heating and cooling system. The apparatus is also provided with a spacer forming an insulating chamber, which provides a stable environment for conducting thermal imaging examination, and a calibration system in form of a stabilized black thermocouple. The spacer in form of a ring or prism with no upper and lower base, and provided with ventilation slots in its side walls is releasably connected to the lower edge of the housing, defining an enclosed space between the housing and the tested skin area, which in turn is defined by a hole in the lower part of the spacer (and more specifically—defined by bottom edges of the spacer). The stationary camera and the thermal imaging camera and the vertically retractable Doppler sensor are mounted directly in the housing, in the central position, which is located directly above the examination field (above the tested skin area). In the lower part of the housing containing the thermal imaging camera, the stationary camera and the Doppler sensor, a rotating tube is provided, driven by a stepper motor, open from both the top and the bottom, with the built-in 3D optical scanner system containing a pattern projector with LED light source, a vertical pattern projection grid and an optoelectronic recorder equipped with a full-spectral digital camera operating in the wavelength range from 300 nm to 1000 nm, whereby both the pattern projector and the recorder are mounted in one plane, inclined with respect to the lower opening of the rotating tube, and the tube itself is arranged on a circular frame allowing circular motions in a plane perpendicular to the optical axis of the thermal imaging camera.

Preferably, the thermal imaging camera system contains at least one or multiple interconnected sensors, giving in total an even number of thermal detectors, preferably uncooled microbolometers matrices, with a native resolution of the thermocouple matrix of at least 640×480.

In another preferable embodiment of the apparatus according to the invention, the thermal imaging camera system (2) is integrated with an optical system consisting of a single or a multi-lens objective with viewing angles of at least 60°×45° providing the pixel size on the skin projected onto the camera matrix not smaller than 0.15×0.15 mm (IFOV—Instantaneous Field of View), and the size of the analytical field consisting of 3×3 pixels not larger than 0.5 mm (MFOV—Measurement Field of View).

Preferably, the thermal imaging camera system (2) is adapted to measure the temperature of tested skin on an area not smaller than 60×150 mm at a distance not exceeding 100 mm.

Preferably, the thermal imaging camera system is provided with an artificial skin master sample setting the emissivity ε of the artificial skin at a level not lower than 0.98, and allowing for setting of the temperature reference point to any value for the temperature range recorded by the thermal imaging camera, but within a range not smaller than 0° C. to 100° C.

Preferably, the calibration system imitating artificial skin, with adjustable temperature and known emissivity (ε) close to a value not lower than 0.98 and preferably close to 1, is mounted on the lower edge, at the inner side of the spacer, within the field of view of the thermal imaging camera and consists of a stabilized heating thermocouple made of resistance material with an electronic temperature regulator operating in a feedback loop with a temperature sensor in form of a thermoresistor, a thermistor or a thermoelectric sensor (thermocouple) allowing precise setting of the temperature point to which the calibration system heats up in respect to the temperature range recorded by the thermal imaging camera.

Preferably, the calibration system imitating artificial skin, with adjustable temperature and a known emissivity (ε) close to 1, is covered with black colour, obtained by using a black pigment, including the one containing micronized carbon or covered with commercially available nanoparticles, e.g. Vantablack supplied by Surrey Nanosystems, having absorption properties for electromagnetic radiation close to a perfectly black body.

Preferably, the spacer is made of plastic, preferably transparent, which allows to illuminate the edges that come into contact with the skin, based on the principle of an optical fiber.

Preferably, the Doppler sensor is equipped with a semiconductor laser producing monochromatic light of the wavelength being at least 560 nm, preferably 780 nm, and having sampling frequency from 10 Hz to 19 kHz, at two bands and with separation of optical fiber channels of at least 46 mm.

Preferably, the stationary camera contains at least one photodetecting matrix with a native resolution of at least 640×480 pixels, selected from CMOS (Complementary Metal-Oxide-Semiconductor) or CCD (Charged-Coupled Device) matrices.

Preferably, the LED (Light Emitting Diode) light source of the 3D scanner pattern projector emits consistent monochromatic radiation in the wavelength range of 380 nm to 780 nm, preferably 415 nm.

Preferably, the heating and cooling system of the apparatus is provided with a directional nozzle to control the air stream in the tested skin area.

Preferably, the spacer is also a chamber for stabilizing the thermal conditions of measurements performed by means of the thermal imaging camera, by closing ambient air inflow to the tested skin surface and directing air from the heating and cooling system directly to the tested skin surface.

The apparatus according to the invention allows for a spectacular improvement of the accuracy and, at the same time the reading reliability of allergy skin tests reproducing both the type I allergic reaction (immediate hypersensitivity) and the type IV allergic reaction (delayed hypersensitivity) by introducing multispectral imaging available through a new and unique combination—within one device—of three digital imaging techniques designed not only to analyse the skin surface, but also the structures located deeper, up to approximately 2000 μm in order to identify: (a) thermal anomalies, so-called hyperthermal allergic reaction, (b) skin surface anomalies appearing as so-called epidermal reaction in Patch tests in form of erythema, papules, vesicles and swelling, and (c) anomalies located in the deeper layer of the skin in form of dilatation of microvessels of subpapillary plexuses in Prick tests in the type I reaction.

The multimodal imaging apparatus according to the invention provides an innovative solution to the above-mentioned problems resulting from using single-mode solutions, including parametric limitations of thermal imaging cameras for medical applications in allergology, as an instrument for qualitative and quantitative analysis of hyperthermic allergic reactions induced by the skin tests, in both variants: Prick tests and Patch tests, however, the anticipated objectivity will be achieved only in combination with (a) laser Doppler flowmetry, which allows for confirming hyperthermia specifically in the Prick tests, and more precisely, its vascular component, by measuring the increased blood-flow in histamine-diluted skin vessels of subpapillary plexuses, and in combination with (b) optical reflectometry of the skin surface in the visible light range, specifically in Patch tests, it additionally allows to precisely identify skin symptoms in form of erythema, vesicles and papules. Accordingly, the apparatus according to the invention jointly generates correlated biophysical data associating: (a) the temperature dimension of allergic hyperthermia, expressed in degrees [° C./F.], with the volume of capillary flow, expressed in flow units [PU] in the microvessels of the subpapillary layer plexuses, which are dilated as a result interaction between histamine released from activated mast cells the type I allergic reaction during Prick tests and endothelial receptors H1, as well as (b) the temperature dimension of allergic hyperthermia, expressed in degrees [° C./F.], with reflectance parameters [°] measured at the affected skin areas where the type IV allergic reaction occurred in Patch tests.

The solution according to the invention is based on the properties of biophysical model of absorption and reflection of diffused light on the surface of skin affected by the allergic reaction, describing the optical characteristics of the occurring phenomena at the photon diffusion level, justifying the use of this model in the construction concept of the optical detector itself, which subsequently, at both hardware and software level, enables objective separation of the area of epidermal anomalies, including allergic erythema highly correlated with hyperthermia, and then precise quantitative representation thereof.

The apparatus according to the invention uses an opto-electronic module constituting the dedicated thermal imaging camera operating in the infrared spectrum (defined as: near—760-4000 nm, mid—4000-14000 nm and far—14000-100 μm) for imaging the thermogenic effect occurring in skin tissue as a result of an allergic reaction induced by applied skin test. The area of epidermally registered subepidermal hyperthermia corresponds topographically to the area where the applied allergen/hapten triggered the allergic reaction accompanied by the hyperthermic reaction, as a result of individual hypersensitivity. The biophysical description of the tissue heat transfer phenomenon forms the theoretical basis for the analytical model allowing to identify the skin areas where the applied allergen triggered a cascade of pathological processes resulting in a significant local increase of skin temperature with an epicenter in the subpapillary layer.

In the optimized biophysical model of heat transfer in the skin tissue, the skin is treated as a multi-layer system comprising an epidermis $\Omega_1$ having non-zero thickness $L_1$-$L_0$, a dermis $\Omega_2$ of non-zero thickness $L_2$-$L_1$ and a subcutaneous layer, considered a quasi-homogenic structure $\Omega_3$ of non-zero thickness $L_3$-$L_2$, where the thermodynamic parameters of these layers are defined as follows: $\lambda_e$ [W/mK] (heat conductivity), and $c_e$ [J/m$^3$K] (specific heat per unit, e=1, 2, 3). The instantaneous biothermal flow in the skin area is described by the following set of equations:

$$x \in \Omega_e: c_e \frac{\partial T_e(x,t)}{\partial t} = \lambda_e \frac{\partial^2 T_e(x,t)}{\partial x^2} + k_e[T_B - T_e(x,t)] + Q_{me},$$

wherein
$k_e = G_e c_B$, and Ge [(m$^3$ blood/s)/(m$^3$ tissue)] is blood/s)/(m$^3$ of tissue)] is the blood perfusion index, $c^B$ [J/(m$^3$K)] is the specific capillary blood volume heat, $T_B$ is the arterial blood temperature and $Q_{me}$ [W/m$^3$] is the metabolic heat source, whereby for the epidermal layer (e=1) $G_1$=0 and $Q_{m1}$=0. The set of equations shall be supplemented by the following boundary conditions:

at the contact surface between the different skin layers considered (e=1, 2):

$$x \in \Gamma_{e,e+1}: \begin{cases} -\lambda_e \frac{\partial T_e(x,t)}{\partial x} = -\lambda_{e+1} \frac{\partial T_{e+1(x,t)}}{\partial x} \\ T_{e(x,t)} = T_{e+1}(x,t) \end{cases}$$

at the standard assumed internal limitations defining the set:

$x \in \Gamma_3: T_3(x,t) = T$ at the skin surface:

$$x \in \Gamma_0: q_1(x,t) = -\lambda_1 \frac{\partial T_1(x,t)}{\partial x} = -\alpha[T_1(x,t) - T_a]$$

where a [W/m$^2$K] is the equivalent heat flow rate, $T_a$ is the ambient temperature. The model assumes that the distribution of initial temperatures is known:

$t=0: T_e(x,t) = T_0(x) e=1,2,3$

Preferably, in order to implement the model for algorithmic analysis in the apparatus according to the invention it is beneficial to use the boundary element method, which for the presented equations and transition states $t^{f-1} \to t^f$ leads to specific formulae for subsequent skin layers, however, the analytical algorithm is not the subject of this application. The thermodynamic model reflects well the phenomenon of bioheat transport through conduction in the skin tissue well, however, it should be noted that recording of epidermal temperature distribution in the allergic reaction induced by the tests concerns the heat flow within the spatial structure of the tissue, the depth (z) of which does not exceed 2.5-2.8 mm, hence the thermal imaging encounters no significant barriers resulting in misleading readings.

In the apparatus according to the invention the registered thermal signatures of local allergic reaction constitute a common factor, but only one of the two analytical factors to be considered in assessment of the results of both Prick and Patch tests. In order to make a complete assessment, it is necessary to use two additional instruments in association with thermal imaging, based on different examination techniques, and confirming the presence of thermal anomalies statistically related to a positive skin allergic reaction.

The first of these instruments is a laser Doppler flowmeter using a low power semiconductor laser emitting a coherent monochromatic light beam of a wavelength in the range optimally from 630 to 780 nm. It plays a confirmatory role in the multimodal allergy imaging system, by identifying increased local blood flow in the vessels of subpapillary layer plexuses, which allows to confirm the origin of the epidermal hyperthermia recorded with the thermal imaging camera, directly resulting from histamine activation of the H1 receptors, leading to dilatation of capillary vessels and is correlated with a positive result of Prick tests.

The second instrument coupled with the thermal imaging camera in the apparatus according to the invention is a 3D skin scanner used for reflectometric measurements. Optical reflectometry in the visible light spectrum wavelength range 380-780 nm, enabling scanning the skin surface and identification of specific eruptions such as allergic erythema, vesicles and/or papules formed during the type IV allergic skin reaction as a result of Patch tests, and is intended to confirm the hyperthermia recorded by the thermal imaging camera in the same tested skin area, which is the first indicator of a positive reaction to applied haptens. The essence of the verification of hyperthermia registered by means of the reflectometric method is to confirm the presence of objective differences in light reflection coefficients in case of a healthy skin and that affected by an allergic reaction, where the anomalies mentioned above occur in form of erythema, papules and/or vesicles, currently assessed in the clinical practice as epidermal symptoms of hypersensitivity inducing the type IV allergic reaction in the test site.

Since in the examining process of biological samples the phenomena of absorption and reflection occur simultaneously, from the hardware perspective and, above all, the measurement perspective (for the purpose of objectivization of the later reading of the allergic reaction area) the priority is to determine the intensity of the reflected beam, which depends on the specific properties of the skin surface.

From the point of view of the biophysical model, when a beam of collimated monochromatic light is reflected by a moving object, in this case the flowing morphotic blood elements, mainly red blood cells, a frequency shift occurs depending on the velocity vector of the moving object, the direction of the incident beam and the direction of the reflected beam. If $k_i$ describes the beam propagation vector (rad/m) for the incident photon and hitting the scattering particle moving at velocity v (m/s), and $k_s$ defines the photon propagation vector reflected from the structure, then the angular shift of frequency $\beta_D$ (rad/s) will be described by the relationship:

$$\beta_D = -v \times q = -v(k_i - k_s) = -\frac{4\pi}{\lambda}|v|\sin(\theta/2)\cos(\varphi)\cos(\alpha),$$

where $\lambda$ is the wavelength (m) for the photon in the surrounding medium, $\Theta$ is the angle of diffusion between $k_i$ and $k_s$, $\alpha$ is the angle between vector v and the diffusion plane, and $\varphi$ is the angle between the projection of vector v in the diffusion plane $a(k_i - k_s)$. The difference between $k_i$ and $k_s$ is defined as the scattering vector q.

Since laser Doppler flowmeter has a very small sampling volume, it becomes sensitive to even minimal spatial changes resulting from perfusion values, and de facto from the flow of capillary blood, and from the optical properties of the tissue. The signal obtained for a specific perfusion at one test site on the same skin test area can change significantly if the measurement site is changed which can be a problem when analyzing the flow within individual points of allergen application. The variability of flow readings may also be characterized by a significant heterogeneity caused by an uneven concentration of blood vessels in the subpapillary layer, to such an extent that the flow signal may differ by approximately one order of magnitude for measuring positions spaced 2.5 mm apart.

The apparatus according to the invention is an innovative hybrid combination of different imaging methods for one pathophysiological condition, i.e. a skin allergic reaction, and furthermore it is adapted to two different variants of allergic reactions: the type I and the type IV. The apparatus according to the invention allows to obtain complementary biophysical data, forming the basis to develop a complex index describing the presence of a positive allergic reaction in both types of skin tests: Prick tests and Patch tests, both in qualitative and quantitative aspect thereof.

The apparatus according to the invention allows to objectively measure the allergic reaction in skin tests using biophysical, rather than biochemical, skin markers of the allergic reaction, of both type I and type IV, measurable by instrumental methods.

Biophysical markers allow in turn for a repeatable and highly standardized multidirectional assessment of the immune response of the skin to the application of test allergens/haptens, which until now was impossible; in particular it was not possible to compare the results of tests performed in different centers, but also at different times in the same center.

The essence of the invention comes down to the innovative use of knowledge about pathophysiological mechanisms accompanying the type I and type IV skin allergic reaction, to produce a hybrid hardware solution meeting the requirements of modern evidence-based medicine (EBM), rather than based exclusively on the individual experience of a physician, which results in significant differences in the accuracy of assessment of the results of skin allergic tests.

The apparatus according to the invention comes down to the construction of a hybrid analyzer combining in a common housing various experimental non-invasive imaging techniques previously known and used separately in allergology, although in terms of unique functional features, it goes far beyond the mere sum of the functionality of the component instruments, because the previously obtained fragmentary measurement data using separate thermal imaging, laser Doppler flowmetry or optical reflectometry did not give clear results. However, their combined use required a prior analysis of the biophysical data characteristics obtained with each of these techniques with respect to determine the way these data will complement each other and whether measurement results will provide the confirmation and accuracy required by the legislations on medical instruments. Confirmation of data obtained in one method is also necessary if it does not provide a hardware solution that would holistically translate measurable parameters of a pathophysiological process into an objective biochemical or biophysical marker. The thermal imaging method is the closest to achieve that aim, but the thermal-optical spatial resolution of the currently used thermal imaging cameras prevents them from being used independently as the sole and exclusive tool for the analysis of allergic skin reaction, that would allow to obtain the required quality of thermal signatures on the surface of the tested skin reaction field.

The apparatus according to the invention provides a dramatic improvement in accuracy and at the same time the reading reliability of the results of skin allergy tests reproducing both the type I and the type IV allergic reaction exactly due to integrating multispectral imaging available through a new and unique combination—within one device—of three digital imaging techniques designed not only to analyse the skin surface, but also the structures located deeper, up to approximately 2000 μm.

The object of the invention is also a method for hybrid imaging of three appropriately selected biophysical parameters characterizing subepidermal allergic reaction during Prick tests, in which the tested section of patient's skin is exposed to allergens and histamine, and also during Patch tests, in which an allergy-inducing substance (a hapten) and an irritant are applied to the tested skin by means of a special Patch. The method according to the invention serves to conduct automatic assessment of biophysical parameters characterizing the allergic reaction, determining in a redundant manner, whether there was a positive allergic reaction at the site of the test application of allergens or haptens as a result of exposing the tested area of the patient's skin to at least one test substance, which in case of Prick tests is an allergen, and in Patch tests—a hapten.

The first component of the hybrid method according to the invention is the determination of the skin field of focal hyperthermia, being a hyperthermic allergic reaction in a skin allergic reaction in case of a positive result of Prick tests, where it is the result of increased perfusion due to posthistamine vasodilatation of the subpapillary microplexuses, as well as Patch tests, wherein the hyperthermia is a result of a complex immune response accompanied by a local inflammatory process with a thermogenic effect; it has a biophysical dimension expressed in Celsius/Fahrenheit degrees.

The second component of the hybrid method according to the invention is the determination of the amount of vascular flow in microplexuses in the subpapillary layer of the skin, which is affected by histamine through activation of endothelial receptors H1, the histamine being released in the type I skin allergic reaction as a result of Prick tests; it has a biophysical dimension expressed in flow units [PU] correlated with the flow rate (mm/s) of the morphotic elements, the blood cells present in the examined vessels, expressed by the dependency $PU=C_{MBC \times VBC}$, where $C_{MBC}$ is the concentration of the moving morphotic blood elements, and $v_{BC}$ is the measured velocity of movement of the morphotic blood elements. The second component is used to confirm the non-artifactuality of the epidermally detected allergic hyperthermia by confirming that its source is a vascular component associated with a posthistamine effect associated with a type I reaction in Prick tests.

The third component of the hybrid method according to the invention is the determination of skin lesions in form of papules and/or vesicles and/or erythema that are formed as a result of a positive type IV skin allergic reaction in Patch tests; it has a biophysical dimension expressed in [mm] and reflects the condition of the tested skin scanned by a 3D skin scanner.

The essence of the hybrid method according to the invention for imaging the parameters of skin allergic reaction in both Prick and Patch tests comes down to the fact that the axis linking the three components of the hybrid method is the thermal imaging, which allows to initially identify the presence of a positive allergic reaction to the epidermally administered test allergens/haptens, thus being a common biophysical determinant (thermal marker) for both types, determining the need for further confirmation of the result of the epidermal hyperthermia tests.

Only the combination of thermal imaging and laser Doppler flowmetry measurements can provide a comprehensive confirmation of a true positive result of a Prick test, eliminating both false negative and false positive results, which is a key parameter that characterizes medical tests in terms of sensitivity and specificity.

Similarly, it is only the combination of thermal imaging and optical reflectometry measurements in the visible light range by means of a 3D scanner that by recording the topography of the skin area covered by the test enables to classify and identify surface skin eruptions resulting from the type IV allergic reaction and thus objectively confirm a positive result of a Patch test, also leading to the elimination of false negative as well as false positive results.

Further, based on the superposition of the thermal imaging results with the results of transdermal laser Doppler flowmetry or optical reflectometry using a 3D scanner, a complete hybrid result is developed, consisting of biophysical indices from individual measurements, allowing to determine the presence and size of allergic reaction in the tested skin area. Compilation of results obtained in individual methods is performed by a specialized computer algorithm, which is not the subject of this application.

Preferably, it is the apparatus for multimodal imaging according to the invention that is used for the physical implementation of the method according to the invention for hybrid imaging of skin allergy reaction parameters.

Preferably, the image of isotherm distribution on the tested skin surface, which is taken by the thermal imaging camera, is digitally imposed onto the visible image of the same tested skin area obtained with a stationary camera.

Preferably, in the method according to the invention for hybrid imaging of allergic skin reaction parameters, before the patient's skin is exposed to at least one allergenic substance, a template is applied to the patient's skin surface for determining the topography of application points of at least one allergenic substance and defining the boundaries of the entire examination area on the skin surface.

The method according to the invention for hybrid imaging of the skin allergic reaction parameters, due to the combination of at least two different measurement techniques: the thermal imaging technique and an optometric technique, being either the laser Doppler flowmetry or the optical reflectometry technique using a 3D skin scanner, provides the required detection reliability owing to the use of other measurement algorithms for imaging different components of the same skin allergic reaction in both the type I allergic reaction in Prick tests and in the type IV allergic reaction in Patch tests, which guarantees that the criteria are met for obtaining a reliable medical test result described by the Received Operating Curve (ROC), which in clinical practice is used as a tool for determining the threshold value of a diagnostic test for which optimal sensitivity and specificity parameters are established.

The method of hybrid imaging of skin allergic reaction parameters determines two complex indices being a parametric combination of measurement results obtained by (a) thermal imaging and (b) laser Doppler flowmetry or (c) optical reflectometry using a 3D skin scanner, dimensioned in arbitrary units: [PTU] for Prick tests and [PATU] for Patch tests.

The arbitrary unit [PTU] is obtained as a logarithmic dimensionless unit, defined according to the formula:

$$PTU = 10\log_{10}\left(\frac{P}{P_0}\right),$$

where P is the size of a complex skin allergic reaction in a Prick test and $P_0$ is a reference size equal to 1, $\log_{10}$ is a decimal logarithm; the size of the complex type I skin allergic reaction is described on the scale presented in Table 1:

TABLE 1

| | | |
|---|---|---|
| for $P_0 = 1$ | PTU = 10 | no allergic reaction in a Prick test - negative allergic reaction; a mean dimension of hyperthermia in [° C./F] correlated with a mean size of an allergic bubble ($W_A$) is equal to or smaller than a mean dimension of hyperthermia in [° C./F] correlated with a mean size of the bubble at a negative control site ($C_N$). |
| for $P_1 = 10$ | PTU = 20 | very poor allergic reaction in a Prick test - very poor positive allergic reaction; the mean dimension of hyperthermia in [° C./F] correlated with the mean size of the allergic bubble ($W_A$) is greater than the mean dimension of hyperthermia in [° C./F] correlated with the mean size of the bubble at the negative control site ($C_N$), and the mean dimension of hyperthermia in [° C./F] correlated with the mean size of the allergic bubble ($W_A$) is less than 1/2 of the average size of a post-histamine bubble ($W_H$) ($C_N < 1/2 W_H$) |
| for $P_2 = 100$ | PTU = 30 | strong allergic reaction in a Prick test - strong positive allergic reaction; the mean dimension of hyperthermia in [° C./F] correlated with the mean size of the allergic bubble ($W_A$) is greater than the mean dimension of hyperthermia in [° C./F] correlated with the mean size of the bubble at the negative control site ($C_N$)., and the mean dimension of hyperthermia in [° C./F] correlated with the mean size of the allergic bubble ($W_A$) is at least equal to the mean size of a post-histamine bubble ($W_H$) ($C_N = W_H$). |
| for $P_3 = 1000$ | PTU = 40 | very strong allergic reaction in a Prick test - very strong positive allergic reaction; the mean dimension of hyperthermia in [° C./F] correlated with the mean size of the allergic bubble ($W_A$) is greater than the mean dimension of hyperthermia in [° C./F] correlated with the mean size of the bubble at the negative control site ($C_N$)., and the mean dimension of hyperthermia in [° C./F] correlated with the mean size of the allergic bubble ($W_A$) is greater than the mean size of a post-histamine bubble ($W_H$) ($C_N > W_H$). |

The arbitrary unit [PATU] is also obtained as a logarithmic dimensionless unit, defined according to the formula:

$$PATU = 10\log_{10}\left(\frac{P}{P_0}\right),$$

where P is the size of a complex skin allergic reaction in a Patch test and $P_0$ is a reference size equal to 1, $\log_{10}$ is a decimal logarithm; the size of the complex type IV skin allergic reaction is described on the scale presented in Table 2:

TABLE 2

| | | |
|---|---|---|
| for $P_0$ = 1 | PATU = 1 | no allergic reaction in a Patch test - negative allergic reaction; mean dimension of hyperthermia in [° C./F] correlated with the dimension of epidermal lesions: no erythema ($A_{PE}$ = 0) no papules ($A_{PP}$ = 0) no swelling ($A_{PI}$ = 0) no vesicles ($A_{VV}$ = 0) is equal to or smaller than the mean dimension of hyperthermia in [° C./F] correlated with the negative index of the presence of skin lesions at the negative control site ($C_N$). |
| for $P_1$ = 10 | PATU = 10 | very poor allergic reaction in a Patch test - very poor positive allergic reaction; the mean dimension of hyperthermia in [° C./F] correlated with the positive index of the presence of skin lesions at the hapten application site ($S_H$). erythema covers less than 70% of the hapten application field ($A_{PE} < S_H$) few papules ($A_{PP} < 5/\text{cm}^2$) poor infiltration/swelling ($A_{PI}$ = 1, on a scale: 1 - weak, 2 - medium, 3 - strong) no vesicles ($A_{PV}$ = 0) and is greater than the mean dimension of hyperthermia in [° C./F] correlated with the negative index of presence of epidermal lesions at the negative control site ($C_N$). |
| for $P_2$ = 100 | PATU = 20 | poor allergic reaction in a Patch test - poor positive allergic reaction; the mean dimension of hyperthermia in [° C./F] correlated with the positive index of the presence of skin lesions at the hapten application site ($S_H$). erythema covers less than 50% of the hapten application field ($A_{PE} < 50\% \, S_H$) few papules ($A_{PP} < 5/\text{cm}^2$) poor infiltration/swelling ($A_{PI}$ = 1, on a scale: 1 - weak, 2 - medium, 3 - strong) no vesicles ($A_{PV}$ = 0) and is greater than the mean dimension of hyperthermia in [° C./F] correlated with the negative index of presence of epidermal lesions at the negative control site ($C_N$). |
| for $P_3$ = 1000 | PATU = 30 | strong allergic reaction in a Patch test - strong positive allergic reaction; the mean dimension of hyperthermia in [° C./F] correlated with the positive index of the presence of skin lesions at the hapten application site ($S_H$). erythema covers more than 75% of the hapten application field ($A_{PE} > 75\% \, S_H$) papules present ($A_{PP} > 5/\text{cm}^2$) |

TABLE 2-continued

| | | |
|---|---|---|
| | | infiltration/swelling present ($A_{PI}$ = 2, on a scale: 1 - weak, 2 - medium, 3 - strong) very few forming vesicles ($A_{PV} > 2/\text{cm}^2$) and is greater than the mean dimension of hyperthermia in [° C./F] correlated with the negative index of presence of epidermal lesions at the negative control site ($C_N$). |
| For $P_4$ = 10000 | PATU = 40 | very strong allergic reaction in a Patch test - very strong positive allergic reaction; the mean dimension of hyperthermia in [° C./F] correlated with the positive index of the presence of skin lesions at the hapten application site ($S_H$). erythema covers more than 90% of the hapten application field ($A_{PE} > 90\% \, S_H$) papules present ($A_{PP} > 7/\text{cm}^2$) infiltration/swelling present ($A_{PI}$ = 3, on a scale: 1 - weak, 2 - medium, 3 - strong) numerous, including overlapping vesicles ($A_{PV} > 5/\text{cm}^2$) and is greater than the mean dimension of hyperthermia in [° C./F] correlated with the negative index of presence of epidermal lesions at the negative control site ($C_N$). |

BRIEF DESCRIPTION OF DRAWINGS

The invention is presented below in a preferred exemplary embodiment, with reference to the attached drawings, on which.

DETAILED DESCRIPTION OF EXEMPLARY EMBODIMENT OF THE INVENTION

Figure 1:
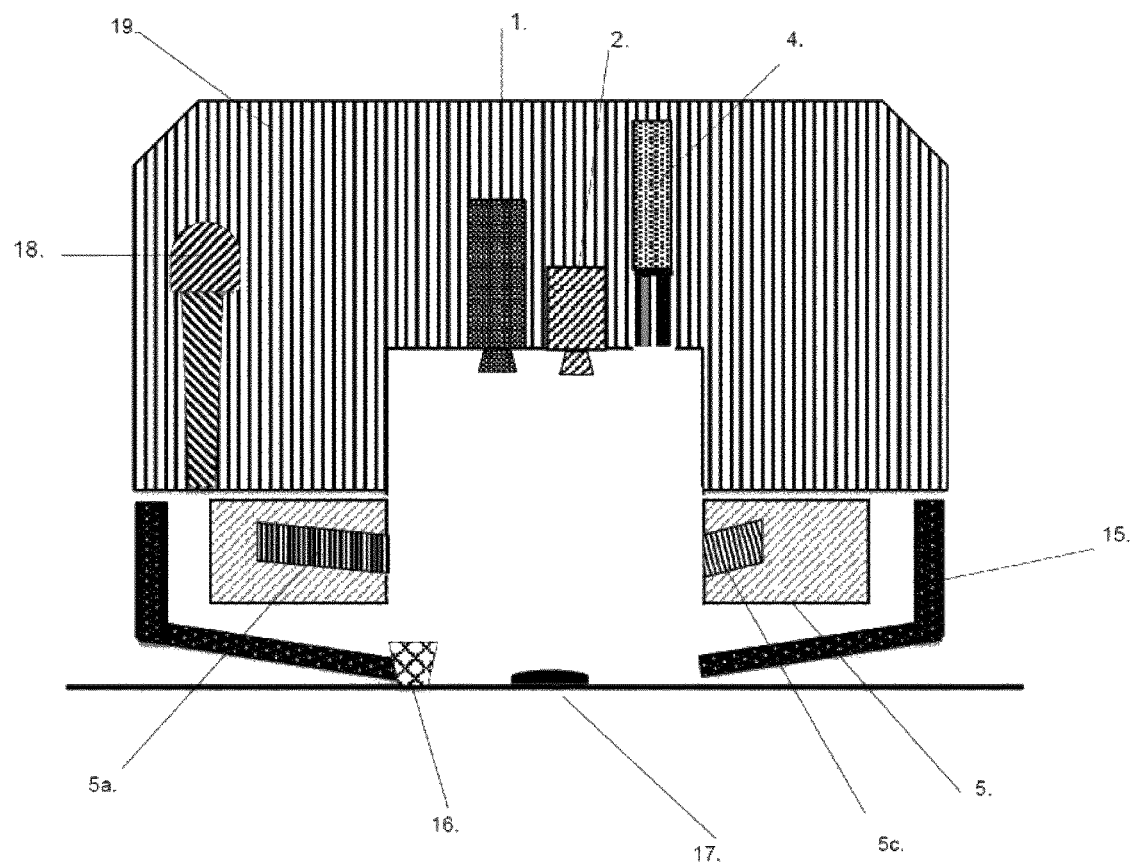
FIG. 1 shows a scheme of an exemplary of embodiment of the apparatus according to the invention.

The exemplary apparatus according to the invention shown in FIG. 1 has a housing 19, in which three measuring instruments are mounted next to each other and directed towards the tested area of skin 17 with a skin lesion resulting from application of an allergen: a stationary camera 1, an infrared thermal imaging camera 2 and a Doppler sensor 4, vertically retractable from the housing. A spacer 15, made of transparent plastic and having an opening defining the field of the skin area 17 to be tested, is attached to the housing 19 facing the patient's skin surface during the examination. During measurement, the spacer 15 rests on the patient's skin surface, ensuring that the instruments are kept at a constant distance from the surface of the tested skin area 17. At the edge of the opening defining the field of the tested skin area 17 the spacer 15 has a heating microelement 16 integrated with a K-type thermocouple in a feedback loop and coated with a black pigment containing micronized carbon or nanotubes commercially available under the trade name VantaBlack™, imitating the thermal and emission standard of artificial skin. During the measurement, the heating microelement 16 is in contact with a fragment of the tested skin area skin 17. The housing 19 is provided with a heating and cooling system 18, providing constant temperature in the immediate vicinity above the tested skin area 17 during measurement. On the underside of the housing of the apparatus, above the tested skin area 17, a tube is provided in form of a rotating ring containing a built-in 3D skin surface scanner 5. Inside the rotating ring of the 3D scanner 5 is an optical system in form of a pattern projector 5a with a LED light source, and a recorder 5c of the 3D skin scanner with a broadband full-spectral digital camera.

Figure 2:
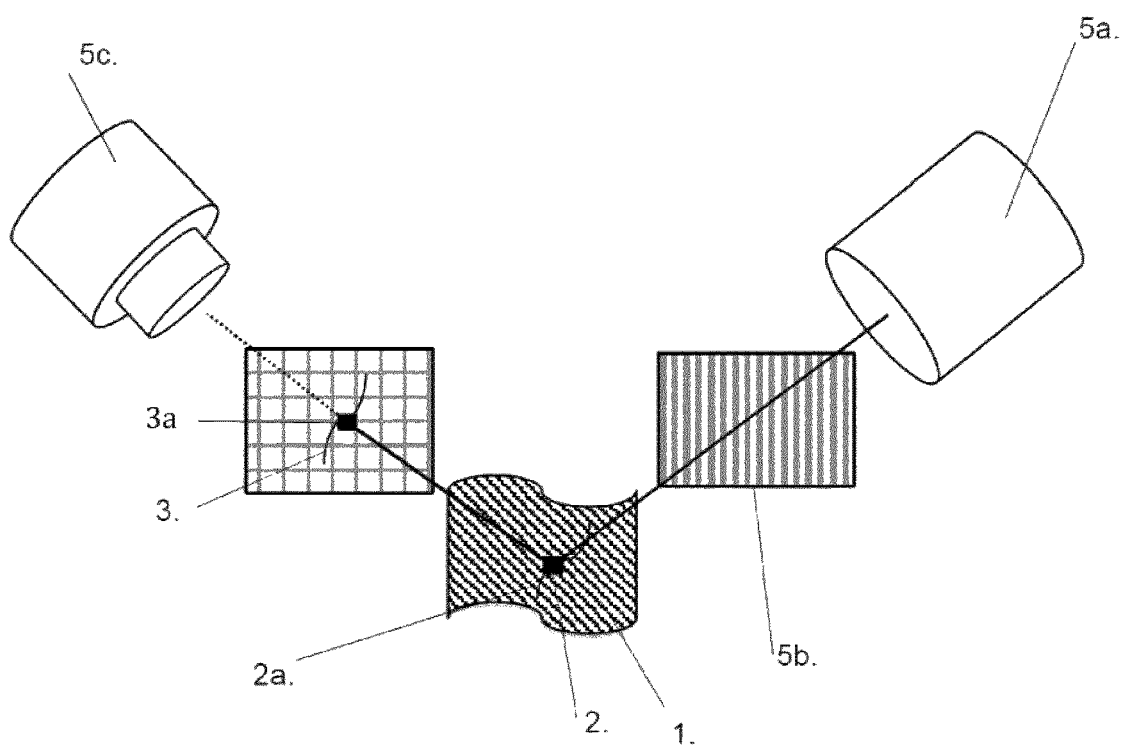
FIG. 2 shows a diagram of a 3D scanner being a part of the apparatus of FIG. 1.

FIG. 2 shows the diagram of the rotating 3D skin surface scanner 5 forming a component of the apparatus according to the invention shown in FIG. 1. The 3D scanner 5 is equipped with a pattern projector Sa with a LED light source, which through a projection grid Sb directs a beam of light in the visible range from 380 to 780 nm to the tested skin area 17. As a result of the light beam passing through the projection grid Sb having a vertical pattern, an image of this pattern is displayed on the tested skin area 17. In case of the presence of papules or vesicles on the skin surface or swelling accompanying the erythema associated with the type IV allergic reaction, a geometric distortion of patterns 2a takes place, so that in the image of reflected radiation registered by the camera matrix of the recorder 5c a representation 3 is formed of distorted patterns on the tested skin area 17. Individual pixels 3a of the photosensitive matrix of the broadband digital camera record the reflected light beam at each scanned point 2 of the tested skin surface 17.

The embodiment of the apparatus according to the invention is related to a complex module for the hybrid comprehensive imaging of biophysical parameters accompanying the skin allergic reaction appearing in both Prick tests and Patch tests, consists of a coupled optoelectronic system integrated in a single housing and containing the following components:
- a thermal imaging camera 2, installed in the central (vertical) axis of a tube formed by a rotating ring at the bottom of the housing; the camera operating in the infrared band in the range of $7.5 \times 10^3$ nm (7.5 μm) to $1.4 \times 10^4$ nm (14 μm), and provided with a dedicated optical system in form of a multi-lens objective; and
- a stationary digital camera 1, operating in the visible light spectrum having the electromagnetic wavelength range from 380 nm to 780 nm, provided with a multi-lens objective;
- a Doppler sensor 4 with a laser operating in a band not lower than 560 nm and optimally 780 nm, with sampling frequency from 10 Hz to 19 kHz, with two optical fiber bands and at least 46 mm separation of optical fiber channels, for transdermal laser Doppler flowmetry (LDF) in the area of vascular microplexuses of the subpapillary layer of the skin,
- a 3D skin scanner 5 consisting of a pattern projector 5a with a monochromatic coherent light source in form of a LED diode and a vertical projection grid Sb used to display patterned images on the tested skin, and a recorder 5c in form of a full-spectral RGB camera operating in a wide spectrum of electromagnetic waves from 300 nm to 1000 nm, in particular covering the visible light spectrum from 380 nm to 780 nm and provided with a multi-lens objective.

A stationary camera 1 operating in the visible light spectrum range is provided with a single matrix or a higher even number of photodetection matrices of CMOS type (complementary metal-oxide semiconductor, composed of MOS-type transistors) having a native resolution of at least 640×480 pixels, or a LIVEMOS variant, or a photodetection matrix of the CCD type (charge-coupled device) having a native resolution of at least 640×480 pixels. From the structural aspect, the 3D skin scanner 5 system consists of a full-spectral camera with a photodetection matrix having a native resolution of 6400×3200 pixels constituting the recorder 5c, together with a pattern projector Sa; in an embodiment the camera 5 with the pattern projector Sa are placed in a single vertical plane, on a movable circular frame moving horizontally with a stepper motor controlled by a computer connected to the apparatus and enabling precise control of yje camera movement over the scanned skin area, so that it would cover the entire tested area with its own field of vision, while also acting as a precise recorder of deformations of the patterns displayed on the skin by the projector Sa. The optical system of the 3D skin scanner 5 is designed to provide minimum scanning parameters with a spatial resolution of at least 0.1 mm, measuring point densities from 0.01 mm to 0.61 mm with a minimum scanning size of 0.03 mm of the scanned skin surface object.

In the embodiment of the apparatus according to the application, the movement of the full-spectral camera used as a recorder 5c, takes place on a circular track of 6.2832 rad (360°) and is coupled with the patter projector 5a placed in the same line but offset to ensure scanning of the entire tested skin area, with the optical axis of the camera being initially set to 0 rad (0°).

In the embodiment a stationary camera 1 CCD was used with a single photodetector matrix having a native resolution of 6400×3200 pixels moving in a horizontal plane on a circular frame with an angle of 6.2832 rad (360°), with the optical axis of the camera initial setting being 0 rad (0°). The stationary camera 1 CCD is moved on this frame by means of a stepper motor controlled by a microprocessor of a PC, to which the apparatus is connected via an USB 2.0 or higher, after starting the 3D scanning sequence of the tested skin surface.

The stationary camera 1 with a CCD matrix is placed in the housing 19 which is open from the bottom towards the tested skin surface, providing the possibility of taking a digital photograph of the tested skin area with a minimum size of 60×150 mm. Preferably, the inner side of the optical system housing 19, in which the lens of the CCD camera is placed, is covered with a black anti-glare layer.

Centrally in the axis of the tube formed by a rotary ring at the bottom of the housing 19, next to the stationary camera 1 CCD, there is an additional thermal imaging camera 2, operating in the infrared range of electromagnetic wavelengths from 7.5 μm to 14 μm, containing one or higher, even number of microbolometers, cooled or uncooled, having a native resolution of at least 640×480 pixels. The thermal imaging camera 2 used in the embodiment of the apparatus according to the invention is permanently fixed in the housing, perpendicularly to the open surface of the housing 19 and preferably has an uncooled microbolometers with a minimum resolution of 640×480 pixels, with a multi-lens objective providing a distance of 100 to 150 mm, minimum required viewing angles of 53°×38° and including a rectangular measuring field of 111×157 mm and a diagonal of 192 mm, while the thermal imaging camera optics ensures adequate geometric resolution, where the size of the minimum segment of the measuring field projected onto a single pixel of the microbolometer is 0.33×0.33 mm (iFOV=0.33 mm) and MFOV=0.99 mm. These values are essential for correct and sufficiently detailed representation of minimum temperature changes at the programmed resolution of the thermal imaging camera 2, directly on the test surface and with maintained integrity of measurement across the entire required test field, the dimension of which is implied by the size of a standard Patch test chamber with sides of approx. 50×140 mm, in which allergenic substances are placed and then attached to the skin, as the dimension of the test field in Prick tests depends exclusively on the physician's decision, who can use either a lancet of pre-determined size or disposable lancets allowing to freely determine the limits of the test field.

If the distance from the optical center of the lens of the thermal imaging camera 2 to the test surface is greater than approx. 150 mm, it may turn out that the actual spatial resolution of the thermal image will be insufficient, and more specifically that the size of a single segment of the test field distinguishable by a single pixel on the microbolometer, for which the thermal imaging camera 2 is able to determine the minimum factory set temperature difference, may prove to be much greater than 1 mm×1 mm, in particular greater than 3 mm×3 mm. Appropriate selection of optics in connection with the minimum thermal resolution of the thermal imaging camera 2 at a level <30 mK with mean measurement error of the thermal imaging camera 2 at around 1% or 1° C., is possible by applying coupled focal length calculation for the objective, at a specified size of the microbolometer and the test field size, according to the formula:

$$O_d = \frac{M_d \times D}{f}$$

where $O_d$ (Object dimensions) is the edge dimension (height or width or diagonal) of the tested quadrilateral object in mm, distinguishable by a single pixel of the microbolometer, f (focus) is the focal length of the objective lens in mm, D (distance) or MOD (minimum object distance) is the minimum distance in mm of the optical center of the objective from the test field, MD (Matrix dimensions: height, width, diagonal) is the dimension of the rectangular microbolometer (height, width, diagonal) in mm.

Calculation of the above parameters allows to solve the problem of insufficient spatial resolution of thermal imaging camera 2, which in known solutions based exclusively on thermal imaging methods was a barrier to correct identification of epicenter of epidermal hyperthermia associated with the application of allergens/haptens and resulted in the fact that despite meeting the technical criteria, thermal imaging cameras used alone were not suitable for biomedical purposes and for imaging of minimal epidermal thermal changes with an accuracy of minimum 0.1° C.

In order to ensure the accuracy of temperature representation in the field of view during each subsequent measurement using the thermal imaging camera 2, it is necessary to place in its field of view one or more calibration standards in form of a heating microelement 16 integrated in the K-type thermocouple feedback loop and covered with a black pigment, including the content of micronized carbon or nanotubes commercially available under the trade name VantaBlack™ imitating the thermal and emission standard of artificial skin, with a surface temperature determined as precisely as possible, facing the objective lens of thermal imaging camera 2, and having emissivity preferably close to 1. The standard of temperature and emissivity, in particular in form of a heating microelement 16, is quadrilateral in shape, with minimum dimensions of 3×3 mm, optimally 10×10 mm. Before each test, the thermal imaging camera 2 should be individually calibrated independently of the factory calibration, setting the emissivity as close to 1 as possible or exactly to 1, and using the black heating microelement 16 as the standard to validate this emissivity setting. If two or four standards are used instead of a single emissivity standard in form of the black heating microelement 16, they should be affixed at the vertices of the test field rectangle so that they additionally serve as topographic markers to superimpose a thermal image on a digital image from the CCD stationary camera 1. For the sake of better visibility of these markers in the infrared thermal imaging camera 2, they should be cooled or warmed by a minimum of 1° C. relative to the mean temperature of the tested skin area 17 before being affixed to the skin.

Initiating the thermal imaging camera 2 test involves attaching a suitable plastic spacer 15 to the device housing 19 by pressing the button activating the device (e.g. marked as "TERMO SCAN"). The tested skin area 17 is the area on which the Prick or Patch tests were previously performed. The start of the thermal imaging test is signaled by a sound and flashing of an appropriate (e.g. green) signaling LED on the device housing. At the same time, a photograph of the tested area is also taken by the stationary camera 1. Positioning the device on the skin is performed manually according to the reference points applied with an appropriate template, with a preview of the image from the stationary camera 1 on the screen of the computer connected to the device. Termination of the thermal imaging test is signaled by a sound and the flashing of an appropriate (e.g. red) signaling LED on the device housing. In the exemplary embodiment the test results are saved in bmt graphic file format with the option to export to jpg, png, csv or xls formats, in the internal memory of the device and on a removable micro SD card, then transferred via USB to a computer, where they are further processed by means of dedicated software, which is not the subject of this application. The results of thermal imaging analysis are displayed in form of jpg or gif graphic files, and in a numerical format indicating the thermal dimension of the recorded hyperthermia areas on the skin surface in ° C. [or ° F. —depending on the user's preference], while the thermal image can be favorably superimposed on the image recorded by the stationary camera 1 in jpg format to highlight a greater number of details of the allergic reaction at the test site. In the applications of the apparatus according to the invention, the measurement of temperature distribution on the tested skin surface is carried out using the differential method, wherein the reference temperature on the material containing the black emissivity standard is measured first.

As already mentioned above, attaching the special spacer 15 in form of a plastic ring or a prism having neither upper nor lower base to the device housing 19 ensures repeatable measurement conditions using the apparatus according to the invention, in particular the appropriate distance between the optical system and the tested surface, resulting from the focal length of the objective lenses used in the CCD stationary camera 1 and the thermal imaging camera 2. Preferably, the spacer may be transparent and additionally contain ventilation slots allowing the heated or cooled air to be released from above the tested skin surface. Preferably, the minimum distance from the tested skin surface to the bottom lens of the optics of the CCD stationary camera 1 and the thermal imaging camera 2, once the distance element 15 is inserted, is 100 mm, and optimally 150 mm. The size of spacer 15 results from the housing variants used and can be, for example, in form of a ring 15a having a minimum diameter of 30 mm and a minimum height of 100 mm (optimally 150 mm) from the center of the optics of the CCD stationary camera 1 and the thermal imaging camera 2, or a prism having neither upper nor lower base 15b having dimensions implied by the minimum size of the test field, i.e. 50 mm×150 mm, but it is also necessary to use an interchangeable, narrowed variant of the spacer 15c in form of a cuboid having neither upper nor lower base, for which its dimension at the contact point with the skin shall be reduced to: minimum width of 30 mm and minimum length of 150 mm. An additional function of the spacer 15 is to provide stable thermodynamic parameters during the thermal imaging test, as it prevents uncontrolled air flow as a cooling/heating medium between the skin and the thermal imaging camera. Moreover, the spacer 15 in combination with the heating and cooling system 18 and the temperature sensor: either a contact one—in form of a thermocouple or thermistor, or a contactless one—in form of a pyrometer or a system with a thermal imaging camera, allows to trigger a forced euthermia on the surface tested skin, controlled by means of feedback from the temperature sensor. In the exemplary embodiment of the apparatus according to the invention, the temperature sensor function is performed by the thermal imaging camera 2, which, before registering the proper thermal imaging sequence, performs a thermal pre-scan, using it as a basis for determining the average temperature of the tested skin area 17.

The controller of the heating and cooling system 18 located in the housing 19 initiates the process of cooling or heating the test area with a stream of air until the average temperature of the test skin area 17 reaches the optimum level for the test. It should be borne in mind that the absolute value of the optimal temperature is individually variable and depends on individual features, while the temperature optimization is carried out by an algorithm implemented by a computer, which is not the subject of this application.

In order to standardize the registration of biophysical parameters in conjunction with the topography of allergens/haptens application points on the skin, it is advantageous to use a template according to which allergens are going to be applied to the tested skin in Prick tests, or the adhesive chambers or patches with haptens are going to be arranged in Patch tests, and according to which the test field boundaries on the skin are going to be marked. A special, appropriately attested hypoallergenic marker should be used for marking points and boundaries according to the template. The template shall be made of a rigid material as biologically neutral for human skin as possible, e.g. plastic or cellulose pulp and shall have dimensions equal to those of the test field corresponding to the test field in Prick and Patch tests. In case of Prick tests, optimally two types of templates: linear and non-linear, are used. The first template enables marking of allergen application points in a narrower field having a width defined by vertices of equilateral triangles with sides equal to min. 30 mm or more and having a minimum length of 150 mm. The second template shall be a rectangle having dimensions of at least 50 mm×150 mm, with holes arranged linearly in two rows with a distance between the centers of the holes of at least 30 mm. For Patch tests, it is optimal to use only the second template type, i.e. a rectangular template with minimum dimensions of 50 mm×150 mm.

Using a template requires placing it on the tested skin area, outlining the contours of the template with a special marker and marking allergens/haptens application points through the holes in the template. The template is not used to standardize the performance of skin tests, nor is it an auxiliary instrument to perform the allergy tests as such, but only to standardize the imaging of biophysical parameters already revealed in allergy tests in the infrared band, so that it is possible to make topographically accurate reference of allergen/hapten application points and the negative and positive control sites, as well as irritant application points, where the thermal camera 2 recorded a local hyperthermia. Hyperthermia is defined as the local temperature in the test field which is at least 0.1° C. higher than the temperature recorded in the test field at the application site of so-called negative control site in form of a saline or glycerin solution, without the addition of allergens, haptens, histamine or any irritants, where $t_{hiper} > 0.1 + t_{contr}$, where $t_{hiper}$ is hyperthermia in ° C., $t_{contr}$ is the temperature at the negative control site in ° C.

The template is used to integrate, i.e. precisely superimpose, a digital image from the CCD stationary camera 1 onto the digital image from the thermal imaging camera 2 to obtain a virtual image of skin lesions in form of allergic reaction symptoms associated with a visualized isotherm distribution on the skin around these lesions, as well as around places where no allergic skin reaction occurred, and sites of the negative control performed using saline or glycerin solution and the positive control using histamine hydrochloride solution (at a dilution of 1:1, 1;10 or 1:1000), and test sites using an irritant. Such a complex virtual image is only used as a starting point for further, more accurate testing using a set of sensors integrated in the apparatus housing 19. These sensors record parameters for specific pathophysiological anomalies associated directly with type I allergic skin reactions triggered by test application of allergens in Prick tests, wherein to confirm the epidermally registered hyperthermia, as induced by a specific allergen, it is necessary to confirm its source, i.e. dilated vessels of subcutaneous microplexuses including subpapillary plexuses as a result of activation of the H1 receptor by histamine released from the granulation of mast cells induced by the allergen applied. Such confirmation is performed by examination of increased flow in these expanded microvessels by transdermal laser Doppler flowmetry using a Doppler sensor 4.

In case of Patch tests reproducing the course of type IV allergic skin reaction, the thermal image due to the inaccuracy of determination of the autonomic marker of this reaction in form of focal hyperthermia, resulting from the very small distance (only 5 mm) between the samples of the tested haptens and therefore the possibility of overlapping isotherms from two different allergic foci, an additional, redundant, objective determination of the presence of other typical allergy indicators in form of epidermal lesions visible as small vesicles and papules, by using 3D scanner 5 imaging of the skin surface, is necessary. The use of multispectral imaging in a single device not only constitutes a measurement redundancy, but also aims at cascade confirmation of the results of the initial imaging of thermal parameters of the skin allergic reaction in the infrared band by dimensioning specific biophysical parameters of the other components of the skin allergic reaction, the measurement of which requires completely different techniques, separate for type I allergic reactions in Prick tests and for type IV reactions in Patch tests. The mechanism of sequential multispectral imaging in skin allergy tests according to the invention effectively solves the problem of full objectivity of their reading by introducing specific biophysical quantities that can be measured and relate to specific response indicators. The analytical model assumes two-stage confirmation of the presence of hypersensitivity to the tested allergen/hapten, firstly by means of the analysis of the test field in infrared—this is a technique common for both type I and type IV allergic reactions. Then, the measurement of particular pathophysiological specific indicators is performed adapted to the type I allergic reaction, where increased local vascular flow is measured in dilated microvessels of skin plexuses, using laser Doppler flowmetry, confirming the effect of histamine release on H1 receptors located in the endothelium. Similarly, in case of type IV allergic reaction, the presence index of epidermal eruptions in form of vesicles and papules, which are currently the basis for differentiation the allergic reaction, is measured. For this purpose, the apparatus employs the method of reconstructing the surface of the skin in a coherent light using a 3D scanner 5, which allows determining the size of these eruptions in mm.

In the exemplary embodiment of the apparatus according to the invention, another integrated measuring instrument arranged in a common housing is the 3D optical scanner system 5, which consists of a mobile recorder 5c in form of a full-spectral camera with a high resolution CCD photodetector having a minimum resolution of 640×480 pixels, working in a wide range of light spectrum from 300 nm to 1000 nm, as well as a movable pattern projector 5a having a light source in form of an LED emitting coherent monochromatic blue light of a wavelength of at least 415 nm and a vertical projection grid 5b enabling to project vertical patterns on the skin surface at a density of at least 10 lines per 1 cm, and an objective lens having a focal length of at least 7.7 mm, allowing to project patterns at the entire tested field with a diameter of at least 30 mm. The 3D optical scanner unit in form of the pattern projector 5a and the recorder 5c is placed in the movable lower part of the housing 19 of the apparatus according to the invention, open on the side facing the tested skin, on a circular frame moving by means of a stepper motor controlled by a computer processor, to which the entire apparatus is connected, enabling strictly controlled movement of the camera recorder 5c in the horizontal plane, allowing for three-dimensional 360° scanning of the tested skin surface.

The analysis of skin lesions in form of vesicles and papules formed in type IV allergic reactions in Patch tests in form of 3D scans requires an appropriate reconstruction of the depth of the obtained epidermal image, which actually means the reconstruction of the depth corresponding to the detected intersections of virtual planes and rays. The result of the calculation is a set of coordinates of intersection points in the global coordinate system (X; Y; Z), where h, v are the coordinates of the detected intersection point and where n is the sequence number obtained in the indexing phase, corresponding to the plane intersecting the point. Then, a computer can generate an equation for this plane (An, Bn, Cn and Dn coefficients), as well as the directional coefficients of the ray corresponding to this point of the 3D scan image ($\Delta$xh and $\Delta$yv). This data is further used to solve the equation of the plane xh,v and yh,v from the system of equations of the ray: 0=An·$\Delta$xh·zh,v+Bn·$\Delta$yv·zh,v+Cn·zh, v+Dn, where the solution is the depth of the point relative to the apparent focal length of the objective of the camera recorder 5c (the origin of the coordinate system), whereby the point is considered determined correctly only if zh,v is positive.

In the solution according to the invention, it was assumed that the final effect of the 3D scanner 5 operation is the reconstruction of the tested skin surface, including the adjustment of the surface to the reconstructed point cloud. As the point cloud projection onto the image sensor of the camera recorder 5c is given and it is known that normal point vectors have a z component facing the direction of the objective lens, a solution is possible in two dimensions, by creating a planar graph connecting the points of the projection, which is optimal in comparison to the reconstruction of the topology of the object examined from the point cloud without such a projection. Based on the vertices and edges data, it is possible to create a triangular area for each three points that are connected to each other. The result of this step is an expected three-dimensional skin surface model with possible eruptions in form of vesicles or papules, however this model does not take into account areas that are not visible from the point of view of the objective lens. In the exemplary embodiment, the scans are saved in the Wavefront OBJ format. The coupled optics system of the 3D scanner 5, consisting of the pattern projector 5a and the recorder 5c, must be capable of reproducing objects on the skin surface by ensuring proper movement of the scanning system. In the exemplary embodiment of the apparatus according to the invention, the coupled optical system of the 3D scanner 5 was placed on a frame in the lower part of the cylindrical housing of the apparatus, so that it can rotate around the vertical axis by 360°, thus ensuring that the 3D scan covers the entire area of the tested skin surface having a minimum diameter of 30 mm. The angular alignment of the optical axis of the projector objective lens 5a and the recorder objective lens 5c must take into account the direction of the light stream reflected from the surface of the tested skin area 17, onto which vertical patters are projected by means of the pattern projector Sa. The measuring ranges of the 3D scanner 5 in the example are in the range for the Z axis: 30 mm minimum, for the X axis: 30 mm, linearity (Z axis): +/−0.2% of range, resolution (Z axis): +/−0.04% of range, linearity on X and Y axes: +−0.4% of range, resolution on X and Y axes: up to 1024 points/profile.

The lens of the digital recorder 5c of the 3D scanner 5 introduces geometric image distortions, so it is necessary to correct the distortions of this device's objective lens, where d is a differentiated distortion function, which assigns a point on an image sensor with coordinates ($h_1$, $V_1$) to each point (h, v) of the image (perspective projection with the center in the apparent focal length of the objective lens). Then there is also the reverse function d−1, which in turn assigns the corresponding points of the image to the matrix points. The correction of distortions is therefore reduced to transforming the coordinates of the matrix point using the function d−1. Distortion correction can be performed either in the scanner or using an external program. The former solution has the advantage of avoiding additional numerical errors when interpolating new pixel positions. A fourth-degree polynomial of the r variable, which is the distance from the center of the image, is most commonly used as the function d. Parameters for this polynomial can be obtained automatically by means of heuristic databases from scanned standards, which was used in the design solution of the apparatus according to the invention.

Activating the 3D scanning sequence involves connecting the spacer 15 to the apparatus housing 19, pressing the start button (e.g. "Patch test 3D scan") and is applicable to a single skin area 17 to which a hapten was previously applied in a Patch test. The start of the 3D scan is signaled by a sound and flashing of an appropriate (e.g. green) signaling LED on the apparatus housing 19. The termination of the 3D scan is signaled by a sound and flashing of an appropriate (e.g. red) signaling LED on the apparatus housing 19. In the exemplary embodiment, the 3D scan results are saved in the Wavefront OBJ format in the apparatus's internal memory and on a microSD card, and then transferred via USB to a PC, where they are further processed by a dedicated software, which is not the subject of this application. Results of the analysis of 3D scans are displayed in form of reconstructed jpg or gif graphic files, and in a numerical format indicating the number of registered skin lesions, their type, and extrapolated dimensions in mm.

In the exemplary embodiment of the apparatus according to the invention, the last integrated measuring instrument placed in the common housing is a Doppler sensor system 4 with a laser working in the band of 560 nm minimum, and optimally 780 nm (i.e. in the near infrared range) having a minimum power of 1 mW, with optical fiber channel spacing of at least 0.25 mm, designed for transdermal laser Doppler flowmetry in the skin microvessels of the subpapillary layer and deeper vascular branches supplying blood to subpapillary plexuses in the tested skin area 17, where Prick tests were previously carried out. Integrating the Doppler sensor 4 in the apparatus according to the invention is dictated by a necessity of ensuring the required measurement redundancy confirming the allergic vascular hyperthermic reaction recorded by the thermal imaging camera 2 and triggered by stimulation of H1 receptors of the endothelium by histamine released from the granulation of mast cells when a positive result of a Prick test is obtained.

Transdermal laser Doppler flowmetry allows only to measure the average flow velocity in skin microvessels and the strength of the signal called blood cell flux, proportional to the product of the number of cells within the tested tissue fragment and the cell movement velocity, the result being expressed in so-called perfusion units (PU), however, the test does not provide a fully objective result as it does not measure the actual flow within the unit: 1 g of blood/100 g of tissue/1 minute. Transdermal laser Doppler flowmetry is of a comparative nature and presents the change in flow in a given vascular bed under the influence of various stimuli. In the apparatus according to the invention, this stimulus is the vasodilatation effect of released histamine on H1 endothelial receptors. Therefore, the use of the Doppler sensor 4 plays a confirmatory role, and the test result is correlated with the results of the thermal imaging test, confirming the connection of the recorded focal epidermal hyperthermia with a co-located increase in flow in microvessels in type I allergic skin reaction triggered by Prick tests.

The Doppler sensor 4 consists of a vertically retractable (by means of a stepper motor) cylindrical head containing optical fiber emitter and receiver-recorder of the beam reflected in the tested tissue, placed inside the apparatus housing at a distance of at least 10 mm from the geometrical center of the housing, as it results from prior experimental works that in case of the examining flow in skin microvessels using this method, in type I allergic skin reaction connected with posthistamine vasodilatation (Hovel et al. *Laser Doppler flowmetry for determining changes in cutaneous blood flow following intradermal injection of histamine, Clin. Allergy*, 17; 1987), the results of measurement at the very point of application of the histamine test, or of the allergen in Prick tests, are inconclusive; optimal flow rates are measured at a distance >10 mm from the point of application, up to approx. 30 mm.

In the exemplary embodiment of the apparatus of the invention, switching a laser operating in the 780 nm band to a laser emitting light with wavelengths of 560 nm, 570 nm and 580 nm was applied in order to additionally determine the epidermal erythema index $E_i$ at the allergy test area. Determination of the epidermal erythema index $E_i$ is performed by evaluating the degree of monochromatic light beam emitted by the laser absorption by hemoglobin, without absorption by the skin pigment—melanin. The index is computed according to the following formula:

$$E_i = \log_{10}\left(\frac{1}{R_G}\right) - \log_{10}\left(\frac{1}{R_R}\right)$$

where $R_G$ is the mean reflectance for three monochromatic light beams of 560 nm, 570 nm, 580 nm and $R_R$ is the reflectance computed according to the formula:

$$R_R = \frac{R_{650nm} + R_{660nm} + \frac{1}{2}R_{640nm} + \frac{1}{2}R_{670nm}}{3}$$

where $R_{650rm}$ is the reflectance for a 650 nm light beam
$R_{660rm}$ denotes reflectance for a 660 nm light beam
$R_{640rm}$ denotes reflectance for a 640 nm light beam
$R_{670rm}$ denotes reflectance for a 670 nm light beam Starting a test using the Doppler sensor 4 involves connecting the plastic spacer 15 to the apparatus housing 19, pressing an activation button (e.g. labeled "LDF Prick Test") and concerns the single test skin area 17 on which an allergen was previously applied during the skin Prick test. The start of the laser Doppler blood flowmetry is signaled by a sound signal and flashing of an appropriate (e.g. green) signaling LED on the apparatus housing 19. At this point, the probe head positioning is performed manually with a PC monitor preview from the stationary camera 1, and the probe head automatically pulls itself out and stops upon contact with the tested skin surface. Termination of the test using the Doppler sensor 4 is signaled by a sound signal and flashing of an appropriate (e.g. red) signaling diode on the apparatus housing. In the exemplary embodiment, the test results are saved as text files in the device's internal memory and on a microSD card, and then transferred via USB to a PC, where they are further processed by a dedicated software, which is not the subject of this application. The test results are displayed as text files and graphs showing the numerical values of the flow in skin vessels in Perfusion Units (PU), where PU is the quotient of the flowing blood cells concentration and the average blood cells flow rate; in the biophysical dimension 1 PU corresponds to 10 mV.

The invention claimed is:
1. A method for imaging allergic skin reactions during a Prick test or Patch test applied to a tested area of a patient's skin, comprising:
  in the case that a Prick test is applied, recording a hyperthermic component of an allergic Type I reaction occurring at the tested area using a thermal imaging camera and also performing transdermal laser Doppler flowmetry at the tested area;
  in the case that a Patch test is applied, recording a hyperthermic component of an allergic Type IV reaction occurring at the tested area by using a thermal imaging camera and also recording an optical component reflecting a topography of the tested area with identification of surface skin lesions via optical reflectometry using a 3D scanner, and
  based on thermal imaging obtained either by the transdermal laser Doppler flowmetry or the optical reflectometry, developing an indication of the allergic reaction of the tested area.

2. The method according to claim 1 performed with the use of a multimodal apparatus, wherein the multimodal apparatus comprises:
- a hybrid structure, combining, in an open-ended housing:
- a recording system containing the infrared thermal imaging camera operating in the electromagnetic wavelength range from 760 nm to 100 μm,
- a stationary camera with a CCD or CMOS photosensitive matrix, operating in a visible light spectrum within an electromagnetic wavelength range from 380 nm to 780 nm,
- a rotating tube comprising:
- the 3D scanner,
- a Doppler sensor for performing transdermal laser Doppler flowmetry,
- a heating and cooling system,
- a calibration system in form of a stabilized heating black body and a spacer comprising a ring or prism releasably connected to a lower part of the housing, the spacer defining an enclosed space between the housing and the tested area, which is defined by a hole in the lower part of the spacer, the stationary camera, the thermal imaging camera and the Doppler sensor being mounted in the housing above the test area, a lower part of the housing containing the thermal imaging camera, the stationary camera and the Doppler sensor and a stepper motor for driving the rotating tube, the rotating tube being open from both a top and a bottom,
- the 3D scanner comprising a pattern projector with an LED light source, a vertical pattern projection grid and a recorder equipped with a full-spectral digital camera operating in wavelength range from 300 nm to 1000 nm,
- whereby both the pattern projector and the recorder are mounted in one plane, inclined with respect to the lower opening of the rotating tube, and the rotating tube itself is arranged on a circular frame allowing circular motions in a plane perpendicular to an optical axis of the thermal imaging camera.

3. The method according to claim 2, further including the step of digitally applying an image of isotherm distribution of the tested area from the thermal imaging camera to a visible light image of the same tested area registered by the stationary camera.

4. The method according to claim 1, further including the step of applying onto the tested area a template determining a topography of points of application of at least one test substance before the tested area is exposed to at least one test substance is applied.

* * * * *